US 9,801,624 B2

(12) United States Patent
Melsheimer et al.

(10) Patent No.: US 9,801,624 B2
(45) Date of Patent: Oct. 31, 2017

(54) SURGICAL SUTURE DEVICE AND METHODS OF USING THE SAME

(71) Applicant: Cook Medical Technologies LLC, Bloomington, IN (US)

(72) Inventors: Jeffry S. Melsheimer, Springville, IN (US); WenHong Neoh, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 757 days.

(21) Appl. No.: 14/055,183

(22) Filed: Oct. 16, 2013

(65) Prior Publication Data

US 2014/0188138 A1    Jul. 3, 2014

Related U.S. Application Data

(60) Provisional application No. 61/746,712, filed on Dec. 28, 2012.

(51) Int. Cl.
*A61B 17/04* (2006.01)
*A61B 17/06* (2006.01)
A61B 17/00 (2006.01)

(52) U.S. Cl.
CPC ...... *A61B 17/0483* (2013.01); *A61B 17/0469* (2013.01); *A61B 17/0485* (2013.01);
(Continued)

(58) Field of Classification Search
CPC ............ A61B 17/0483; A61B 17/0469; A61B 17/0485; A61B 2017/00367; A61B 2017/06042
See application file for complete search history.

(56) References Cited

U.S. PATENT DOCUMENTS

| | | |
|---|---|---|
| 919,138 A | 4/1909 | Drake et al. |
| 1,167,014 A | 1/1916 | O'Brien |

(Continued)

FOREIGN PATENT DOCUMENTS

| | | |
|---|---|---|
| EP | 2314238 | 4/2011 |
| EP | 2394585 | 12/2011 |
| FR | 2701832 | 9/1994 |

OTHER PUBLICATIONS

Extended European Search Report for EP13199161 dated Nov. 25, 2014, 7 pgs.

*Primary Examiner* — Darwin Erezo
*Assistant Examiner* — Tin Nguyen
(74) *Attorney, Agent, or Firm* — Brinks Gilson & Lione

(57) ABSTRACT

A medical instrument, such as a surgical device for manipulating and placing a tissue suture and methods of using the same is disclosed. The device comprises a handle, a hollow shaft removably coupled to the handle assembly and a stylet extending within the hollow shaft and longitudinally slideable therein. Preferably, the stylet is not rotationally moveable relative to the shaft. The stylet may be moved between a first position wherein a grasping member formed on the stylet is retracted into a distal end portion of the shaft and a second position wherein the grasping member extends distally beyond the distal end portion of the shaft. Distal movement of an actuation member on the handle correspondingly moves the stylet to the extended position and movement of the actuation member to a proximal position on the handle correspondingly moves the stylet to the retracted position. Lateral movement of the actuation member on the handle does not impart rotational movement of the stylet relative to the shaft.

18 Claims, 3 Drawing Sheets

(52) U.S. Cl.
CPC ............... *A61B 2017/0046* (2013.01); *A61B 2017/00367* (2013.01); *A61B 2017/06042* (2013.01)

(56) References Cited

U.S. PATENT DOCUMENTS

| | | | |
|---|---|---|---|
| 2,808,055 A | 10/1957 | Thayer | |
| 3,868,957 A | 3/1975 | Doddington | |
| 4,165,747 A | 8/1979 | Bermant | |
| 4,243,048 A | 1/1981 | Griffin | |
| 4,874,375 A | 10/1989 | Ellison | |
| 5,085,661 A | 2/1992 | Moss | |
| 5,201,741 A | 4/1993 | Dulebohn | |
| 5,281,237 A | 1/1994 | Gimpelson | |
| 5,312,422 A | 5/1994 | Trott | |
| 5,395,382 A | 3/1995 | DiGiovanni et al. | |
| 5,405,354 A | 4/1995 | Sarrett | |
| 5,433,722 A | 7/1995 | Sharpe et al. | |
| 5,439,467 A | 8/1995 | Benderev et al. | |
| 5,458,608 A * | 10/1995 | Wortrich .......... A61B 17/00234 227/110 | |
| 5,474,565 A | 12/1995 | Trott | |
| 5,501,692 A | 3/1996 | Riza | |
| 5,507,758 A | 4/1996 | Thomason et al. | |
| 5,562,685 A | 10/1996 | Mollenauer et al. | |
| 5,562,688 A | 10/1996 | Riza | |
| 5,605,162 A | 2/1997 | Mirzaee et al. | |
| 5,649,939 A | 7/1997 | Reddick | |
| 5,676,675 A | 10/1997 | Grice | |
| 5,709,692 A | 1/1998 | Mollenauer et al. | |
| 5,716,369 A | 2/1998 | Riza | |
| 5,746,753 A | 5/1998 | Sullivan et al. | |
| 5,758,665 A | 6/1998 | Suval | |
| 5,788,716 A | 8/1998 | Kobren et al. | |
| 5,791,699 A | 8/1998 | High | |
| 5,797,929 A | 8/1998 | Andreas et al. | |
| 5,817,112 A | 10/1998 | Christoudias | |
| 5,827,299 A | 10/1998 | Thomason et al. | |
| 5,899,911 A | 5/1999 | Carter | |
| 5,904,692 A | 5/1999 | Steckel et al. | |
| 5,910,148 A | 6/1999 | Reimels et al. | |
| 5,951,067 A | 9/1999 | High | |
| 5,954,734 A | 9/1999 | Thomason et al. | |
| 6,022,360 A | 2/2000 | Reimels et al. | |
| 6,102,920 A | 8/2000 | Sullivan et al. | |
| 6,183,485 B1 | 2/2001 | Thomason et al. | |
| 6,254,620 B1 | 7/2001 | Koh et al. | |
| 6,699,263 B2 | 3/2004 | Cope | |
| 6,723,107 B1 | 4/2004 | Skiba et al. | |
| 6,746,457 B2 | 6/2004 | Dana et al. | |
| 6,770,084 B1 | 8/2004 | Bain et al. | |
| 7,147,646 B2 | 12/2006 | Dana et al. | |
| 7,169,156 B2 | 1/2007 | Hart | |
| 7,311,715 B2 | 12/2007 | Sauer et al. | |
| 7,491,212 B2 | 2/2009 | Sikora et al. | |
| 7,704,262 B2 | 4/2010 | Bellafiore et al. | |
| 7,749,250 B2 | 7/2010 | Stone et al. | |
| 7,803,167 B2 | 9/2010 | Nobles et al. | |
| 7,879,048 B2 | 2/2011 | Bain et al. | |
| 8,066,718 B2 | 11/2011 | Weisel et al. | |
| 8,109,943 B2 | 2/2012 | Boraiah et al. | |
| 8,109,945 B2 | 2/2012 | Boehlke | |
| 8,162,962 B2 | 4/2012 | Poo et al. | |
| 8,460,322 B2 | 6/2013 | van der Burg et al. | |
| 8,496,676 B2 | 7/2013 | Nobles et al. | |
| 8,529,583 B1 | 9/2013 | Golden et al. | |
| 8,562,629 B2 | 10/2013 | Bain et al. | |
| 8,579,921 B2 | 11/2013 | Hathaway et al. | |
| 8,585,714 B2 | 11/2013 | Weisel et al. | |
| 2005/0021055 A1 | 1/2005 | Toubia et al. | |
| 2005/0085831 A1 | 4/2005 | Rioux | |
| 2005/0234481 A1 | 10/2005 | Waller | |
| 2006/0069399 A1 | 3/2006 | Weisel et al. | |
| 2006/0264976 A1 | 11/2006 | Terry et al. | |
| 2006/0270900 A1 | 11/2006 | Chin et al. | |
| 2007/0083235 A1 | 4/2007 | Jervis et al. | |
| 2007/0118152 A1 | 5/2007 | Page | |
| 2007/0118153 A1 | 5/2007 | Funamura et al. | |
| 2008/0097484 A1 | 4/2008 | Lim et al. | |
| 2008/0269784 A1 * | 10/2008 | Abbott ................ A61B 17/11 606/144 | |
| 2009/0259234 A1 | 10/2009 | Waller | |
| 2010/0130989 A1 * | 5/2010 | Bourque .......... A61B 17/0401 606/144 | |
| 2010/0324573 A1 | 12/2010 | Toubia et al. | |
| 2012/0095481 A1 | 4/2012 | Bouduban et al. | |
| 2012/0123448 A1 | 5/2012 | Flom et al. | |
| 2012/0143220 A1 | 6/2012 | Morgan et al. | |
| 2012/0143221 A1 | 6/2012 | Weisel et al. | |
| 2013/0035699 A1 | 2/2013 | Heneveld et al. | |
| 2013/0079597 A1 | 3/2013 | Auerbach et al. | |
| 2013/0116710 A1 | 5/2013 | Ziniti et al. | |
| 2013/0165956 A1 | 6/2013 | Sherts et al. | |
| 2013/0218175 A1 | 8/2013 | Auerbach et al. | |
| 2013/0310856 A1 | 11/2013 | Sherts et al. | |

* cited by examiner

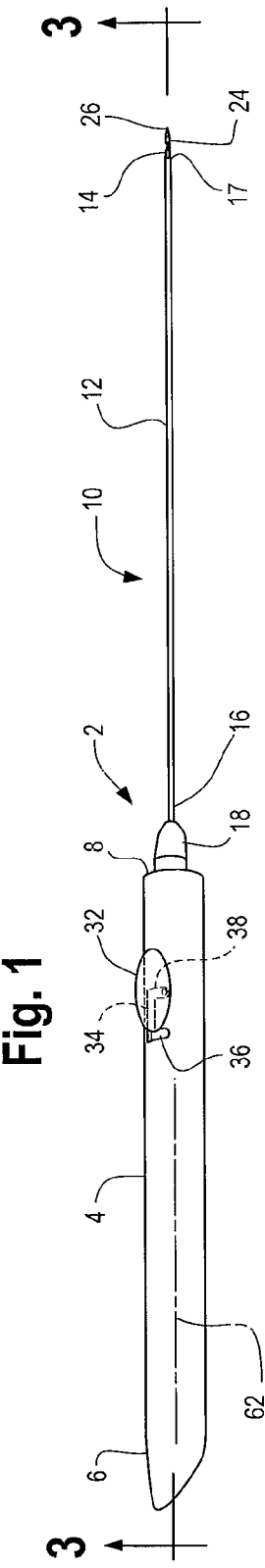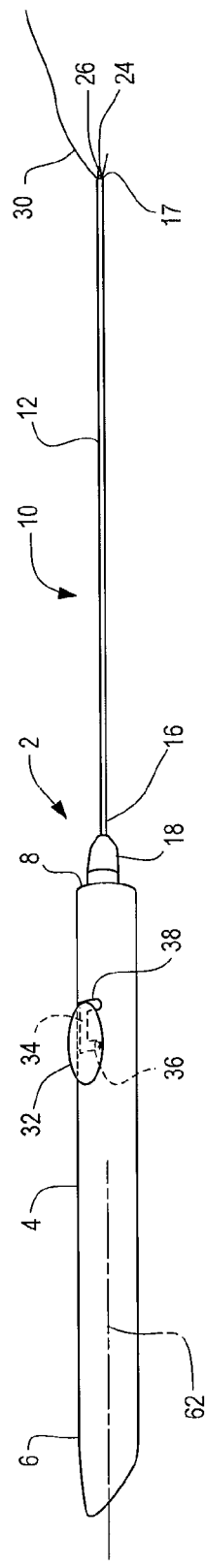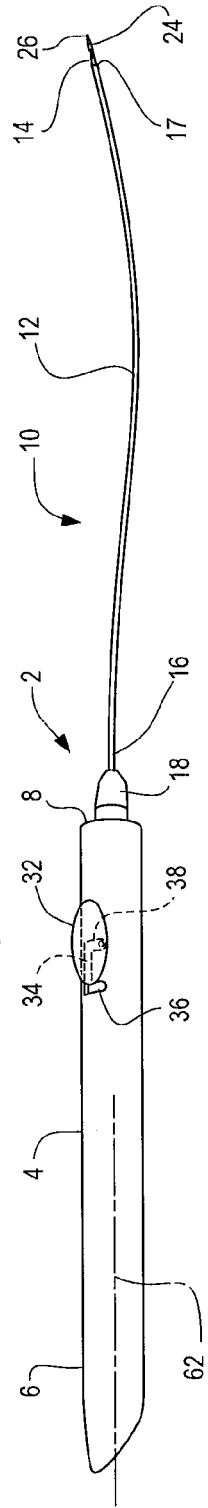

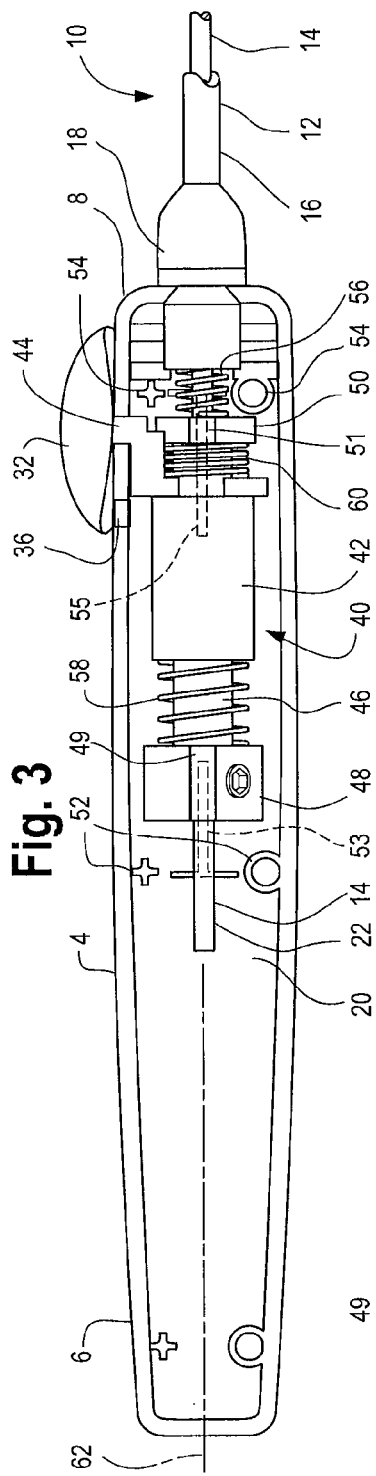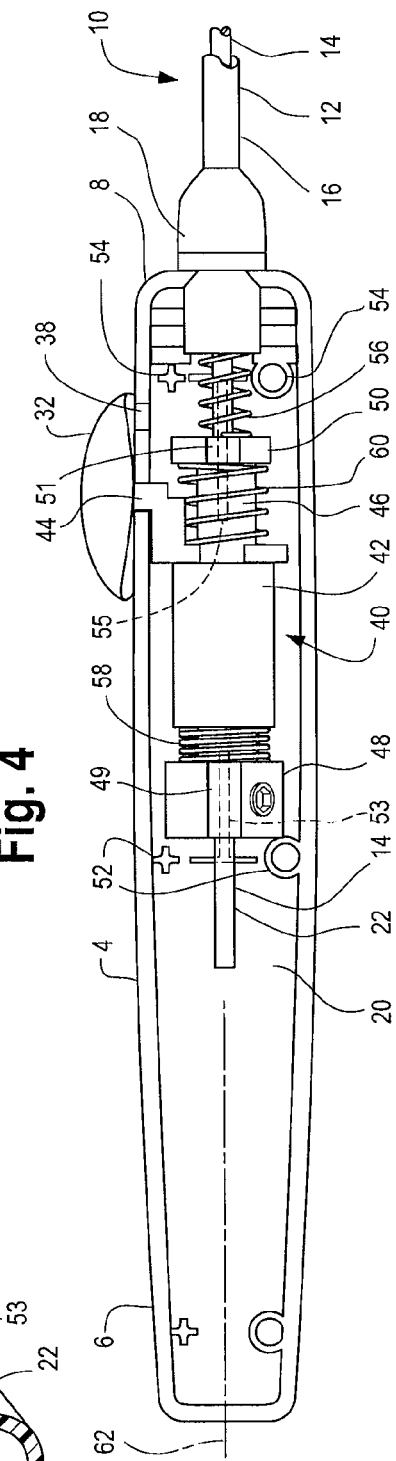

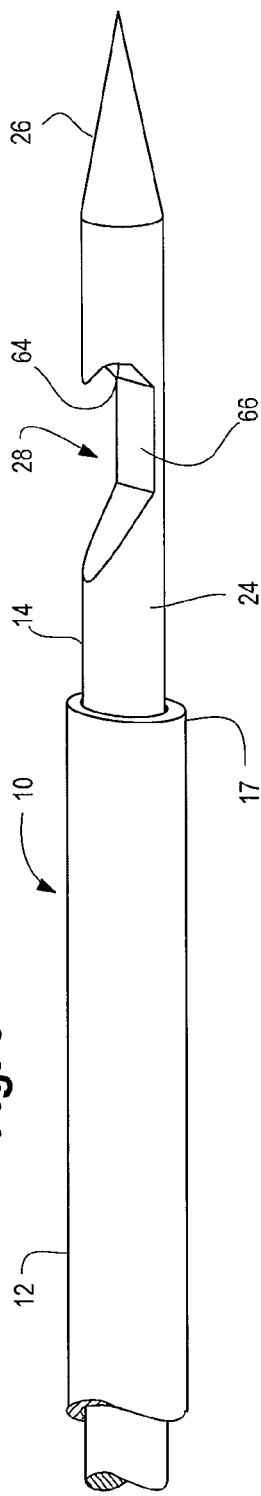
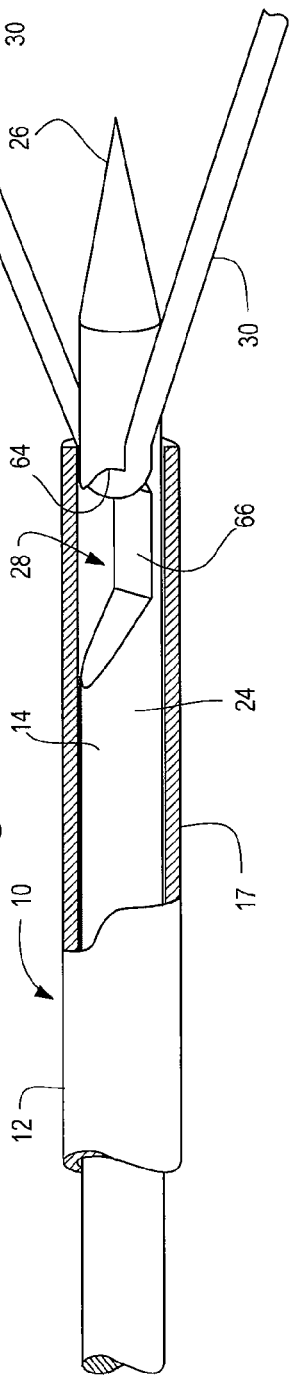

SURGICAL SUTURE DEVICE AND METHODS OF USING THE SAME

RELATED APPLICATIONS

This application claims the benefit of priority of U.S. Provisional application Ser. No. 61/746,712 filed on Dec. 28, 2012, which application is incorporated by reference herein in its entirety.

TECHNICAL FIELD

The present invention relates generally to a medical instrument and more particularly, to a surgical device for manipulating a tissue suture and methods of using the same.

There are a variety of surgical procedures in which it is desirable to place and manipulate sutures in tissues, membranes or in a graft. One particular situation in which suture placement is desired or necessary arises in endoscopic, arthroscopic, laparoscopic and other surgical procedures, including but not limited to a hernia repair, in which sutures are introduced in the interior of the body. Oftentimes, sutures must be positioned in difficult to reach orientations or tissue sites in the body which may possibly result in restrictions on the shape, size and number of the tool(s) used to perform a suture placement procedure and/or lead to an increased complexity and duration of the particular procedure. Therefore, it is desirable to provide a manually operated surgical instrument to access a target tissue location and accurately manipulate and place one or more sutures therein, while minimizing factors such as cost, tissue trauma, user fatigue and/or handling difficulties.

SUMMARY

A medical instrument for manipulating and placing a suture in body tissue is disclosed. In one example, the instrument includes a handle assembly comprising an elongated housing defining an interior chamber and a longitudinal slot formed in the housing. The longitudinal slot has a proximal end and a distal end. At least one lateral slot is also formed in the housing. An actuation member is moveable in the longitudinal slot between a proximal position and a distal position and moveable in the at least one lateral slot between a first lateral position and a second lateral position. The instrument further preferably comprises a hollow shaft having a distal end portion and a proximal end portion removably coupled to the handle assembly, and a longitudinal axis extending between the proximal and distal end portions of the shaft. A stylet extends within the hollow shaft and is longitudinally slideable therein, and preferably, the stylet is not rotationally moveable relative to the shaft axis. The stylet has a distal end portion with a grasping member configured for engagement with a suture and a proximal end portion extending at least partially into the handle interior chamber. The stylet is moveable between a first position wherein the grasping member is retracted into the distal end portion of the shaft and a second position wherein the grasping member extends distally beyond the distal end portion of the shaft. Movement of the actuation member to the distal position within the longitudinal slot correspondingly moves the stylet to the extended position and movement of the actuation member to the proximal position within the longitudinal slot correspondingly moves the stylet to the retracted position. Preferably, movement between the first and second lateral positions does not impart rotational movement of the stylet relative to the shaft.

In another example, a method for using an apparatus to manipulate and place a suture in a bodily tissue is disclosed. In one example, the method preferably utilizes an apparatus having a handle assembly comprising an elongated housing defining an interior chamber and a longitudinal slot formed in the housing. The longitudinal slot has a proximal end and a distal end and at least one lateral slot formed in the housing. An actuation member is moveable in the longitudinal slot between a proximal position and a distal position and is also moveable in the at least one lateral slot between a first lateral position and a second lateral position. A hollow shaft having a distal end portion and a proximal end portion is removably coupled to the handle assembly and has a longitudinal axis extending between the proximal and distal end portions of the shaft. A stylet extends within the hollow shaft and is longitudinally slideable therein, and preferably, the stylet is not rotationally moveable relative to the shaft axis. The stylet has a distal end portion with a grasping member configured for engagement with a suture and a proximal end portion, wherein the actuation member is configured impart proximal and distal longitudinal movement of the stylet relative to the shaft. The stylet has a first position wherein the grasping member is retracted into the distal end portion of the shaft and a second position wherein the grasping member extends distally beyond the distal end portion of the shaft.

In one example, the method of using the exemplary apparatus comprises the steps of penetrating a bodily tissue with the apparatus when the stylet is in the retracted position, moving the actuation member distally within the longitudinal slot to move the stylet to the second distally extended position while rotational movement of the stylet relative to the hollow shaft is prevented, manipulating a suture with the grasping member at the distal end portion of the stylet and withdrawing the apparatus from the bodily tissue.

BRIEF DESCRIPTION OF THE DRAWINGS

FIG. 1 is a side view of one example of a surgical device for manipulating a suture with a stylet in an extended position.

FIG. 1A is a side view of another example of a surgical device for manipulating a suture with a stylet in a retracted position and a suture retained at the distal end.

FIG. 2 is a side view of another example of a surgical device for manipulating a suture with a curved stylet.

FIG. 3 is a side cross-sectional view of one example of the handle portion of a surgical device with the thumb trigger in the distal position.

FIG. 3A is a partial perspective view of the handle portion shown in FIG. 3.

FIG. 4 is a side cross-sectional view of the device of FIG. 3 with the thumb trigger retracted to a proximal position.

FIG. 5 is a perspective view of the distal portion of a surgical device with the stylet extended out of the distal end of the shaft.

FIG. 6 is a partial side cross-sectional view of the surgical device of FIG. 5 with the stylet retracted into the distal end of the shaft and retaining a suture therein.

DETAILED DESCRIPTION

The examples and embodiments described below are primarily in connection with a medical instrument, such as a surgical device for manipulating a tissue suture and methods of using the same, however, the described device may also be used in connection with a range of medical procedures and methods where necessary or desirable as will be appreciated by one of skill in the art. FIG. 1 illustrates one example of a medical instrument, such as a surgical device shown generally at 2. The device includes a handle 4 having a proximal end portion 6 and a distal end portion 8. The handle 4 may be constructed from various materials including thermoplastic and/or polymeric materials such as acrylonitrile butadiene styrene (ABS) polymer. A suture assembly 10 is coupled to the distal end portion 8 of the handle 4. As shown in FIGS. 5 and 6, the suture assembly 10 preferably comprises an outer hollow shaft 12 and an inner actuatable stylet 14 that extends longitudinally within the hollow shaft 12. The shaft 12 and the stylet 14 may be formed from a variety of materials, including, but not limited to stainless steel.

In one example, the shaft 12 preferably comprises a hollow cannula that may be straight or curved shown in FIGS. 1 and 2, respectively, and having a generally circular cross section, although a variety of sizes, shapes and cross-sectional configurations of the shaft 12 may also be used as necessary or desired, depending on the particular intended use of the instrument, the tissue site being accessed, the target suture placement location and/or the procedure being performed. For example, the shaft 12 may be flared, such that it has a larger cross-section or outer diameter at the shaft proximal end 16 where the shaft is mounted on or otherwise secured to the handle 4. As shown in exemplary FIGS. 1, 3 and 4, a portion of the shaft 12 may be captured by a flare fitting 18 to secure the suture assembly 10 at the handle distal end 8. Alternatively, the shaft 12 may be mounted or secured to the handle 4 by various other acceptable methods including adhesive, bonding, welding and/or one or more fasteners. In one non-limiting example, the shaft 12 may have a length of about 15 cm and an outer cross-sectional diameter of about 2.75 mm. Of course, if the shaft 12 is flared, the cross-sectional dimensions may vary along the length of the shaft. It is contemplated that the shaft 12 is removably secured to the handle 4 so that it can be detached and replaced with a shaft having alternate configurations and/or dimensions. While the outer hollow shaft 12 may terminate at or near the point at which it is secured to the handle 4, the inner actuatable stylet 14 may extend farther into the handle interior 20, where it may be mounted or removably secured therein as described in further detail below.

The stylet 14, having a proximal end portion 22 and a distal end portion 24, is disposed coaxially within the hollow shaft 12. As FIGS. 5 and 6 show, the stylet 14 may be a generally solid wire rod or elongated structure that is longitudinally slideable within the shaft 12. In one example, the distal end 24 of the stylet is preferably configured to allow it to pierce, puncture or be pushed or pulled though one or more membrane, graft and tissue layers or perforations formed therein. For example, the stylet 14 preferably terminates in a sharpened tip 26 and includes a recessed "hook" or suture grasping member 28 formed in the stylet 14 located just proximal to the sharpened tip 26. This suture grasping member 28 is preferably configured to snag, grasp and retain a suture 30 therein and facilitate manipulation of the suture 30 during use of the instrument.

As further illustrated in FIGS. 3 and 4, the handle 4 preferably includes a mechanism that can be manually actuated by the user, which facilitates longitudinal movement of the stylet 14 relative to the shaft 12. In one example, such a mechanism includes a thumb-actuated slideable trigger 32, although, other mechanisms may also be used for sliding the stylet within the shaft, such as a knob, lever, rolling wheel or ball, button, slide, switch, and the like. In one example, the stylet 14 is moveable between a distally extended position as illustrated in FIG. 5 and a proximally retracted position as illustrated in FIG. 6. Preferably, mechanisms within the handle interior 20 (which are discussed in further detail below) bias or urge the stylet 14 in the retracted position.

In the extended position, the suture grasping portion 28 extends distally beyond the distal end 17 of the shaft, while in the retracted position, the suture grasping portion 28 is preferably withdrawn inside the distal end 17 of the shaft. Yet, as shown in FIG. 6, even when the stylet 14 is in the retracted position, the sharpened tip 26 of the stylet 14 still preferably protrudes or extends beyond the distal end 17 of the shaft. In this way, the sharpened tip 26 helps the suture assembly 10 to be passed freely through tissue when the stylet 14 is in the retracted position, while the suture grasping portion 28 is covered by the outer hollow shaft 12 and thus preventing the suture grasping portion 28 from snagging or inadvertently tearing the tissue as the suture assembly 10 is passed therethrough.

Turning back to FIGS. 3 and 4, details of one example of the handle assembly 4 is illustrated. As previously mentioned, the handle 4 includes a user-actuated mechanism that facilitates movement of the stylet 14 relative to the shaft 12. Preferably, the mechanism includes a thumb-actuated trigger 32 that slides within in a generally longitudinal slot 34 or channel that is formed in the handle 4 as shown in FIGS. 1, 1A and 2. When the trigger 32 is moved in a forward or distal direction, this causes the stylet 14 to also move distally to extend the suture grasping portion 28 at least partially out of the distal end 17 of the shaft as shown in FIGS. 1, 2 and 5. When the trigger 32 is moved back though the longitudinal slot 34 towards the user in a proximal direction as shown in FIG. 1A, the stylet 14 is retracted back into the shaft 12. The trigger 32 can also preferably be moved laterally or "side-to-side" relative to the handle 4 in one or more lateral slots 36, 38 as shown in FIGS. 1-2. The lateral slots 36, 38 may be located at the proximal-most and distal-most (or both) ends of the longitudinal slot 34. The lateral slots 36, 38 may be generally straight channels formed at approximately 90 degree angles from the proximal and distal ends of the longitudinal slot 34, or alternatively, the lateral slots 36, 38 may be angled, curved or otherwise arranged in different configurations that would also allow for the thumb-actuated trigger 32 to move out of the longitudinal slot 34 and into one of the lateral slots in order to secure or lock the stylet 14 in a particular position relative to the shaft 12.

For example, although the stylet 14 is preferably biased in the retracted position, it may be desirable to lock or at least temporarily secure the stylet 14 in the retracted position. This may be accomplished by moving the trigger 32 laterally within the proximally located lateral slot 36 when the stylet 14 is in the fully retracted position and the trigger 32 in its proximal-most position within the longitudinal slot 34 formed on the handle 4. When the trigger 32 has been moved into the lateral slot 36, the user can relax his grip upon the handle 4 and even release his thumb from the trigger 32 and the stylet 14 will remain locked in the retracted position to prevent unwanted distal movement of the stylet. This may be desirable, for example, when a suture 30 has been grasped by portion 28 during a particular procedure and the user wants to ensure retention of the suture 30 in portion 28 during passage of the suture assembly 10 through tissue and/or when the user wants to release or relax his grip upon the handle 4 or trigger 32 during use but would like to prevent unintentional longitudinal movement of the stylet 14 within the shaft 12.

Likewise, it may also be desirable to lock or temporarily secure the stylet 14 in the distal or extended position, where at least a portion of the distal end 24 of the stylet is exposed and extended beyond the distal end 17 of the shaft as FIG. 5 illustrates. Preferably, the suture grasping portion 28 located at the distal end 24 of the stylet is extended out of the shaft 12 when the thumb actuated trigger 32 is moved forward to its distal-most position in the longitudinal slot 34 in the handle. At this position, the trigger 32 may be moved laterally into the distally located lateral slot 38 as shown in FIG. 3 to lock the stylet 14 in this extended position. This may be desirable, for example, during a portion of a procedure when the suture assembly 10 has been inserted through a target tissue location or perforation therein and the user is trying to manipulate the device 12 and grasp a suture 30 within grasping portion 28 of the stylet. By locking the stylet 14 in the extended position, the grasping portion 28 remains exposed beyond the shaft distal end 17 and is capable of grasping or snagging a suture 30 without the user having to retain his thumb grip on the trigger 32 and manually keep the trigger pushed forward to keep the stylet 14 extended until the suture 30 has been located and grasped. In other words, the user's thumb can be freed from having to engage the thumb trigger 32 and maintain a forward (distal) pushing force thereon. This may have several advantages including, but not limited to, reducing user fatigue, preventing potential slippage or lost grip on the trigger and unwanted or premature retraction of the stylet during the course of a particular procedure.

It can be seen in FIGS. 3 and 4 that the thumb-actuated trigger 32 is part of or is engageable with, an actuatable unit 40. The actuatable unit 40 is, in one example, longitudinally translatable within the handle interior 20 in order to control proximal and distal movement of the stylet 14. In one example, the thumb actuated trigger 32 is secured to, engaged with and/or integrally formed with, a generally hollow cylindrical member 42 that is located within the handle 20. More specifically, a narrowed neck portion 44 extends from the underside of the thumb trigger 32, through the lateral slots 36, 38 and/or longitudinal slot 34 formed in the handle 4, and engages the cylindrical member 42 within the interior of the handle 20. An elongated hollow rod 46 extends through the cylindrical member 42, and the proximal end portion 22 of the stylet extends into the handle interior 20 where the stylet 14 is preferably removably secured to and/or within the hollow rod 46. Together, the cylindrical member 42 and the elongated rod 46 (and the proximal end of the stylet 22 secured to the rod) form an actuatable unit 40 that can be moved longitudinally between a proximal and distal position within the handle interior 20 by movement of the thumb trigger 32 located on the outside of the handle 4 to accurately control the position of the stylet 14 relative to the shaft 12. In other words, distal movement of the thumb trigger 32 facilitates distal movement of the actuatable unit 40 within the handle causing the stylet 14 to move to an extended position, while proximal movement of the thumb trigger 32 facilitates proximal movement of the actuatable unit 40 within the handle causing the stylet 14 to retract within the shaft 12.

As shown in FIGS. 3 and 4, a member is located at or near the proximal and distal ends of the rod and extends radially outwardly from the rod 46, thus providing a "stop" on each end of the rod. The members or stops 48, 50 may be integrally formed with the rod 46 or, alternatively, one or more of the stops 48, 50 may be separately molded structures that are secured to the rod such as by bonding, adhesive, one or more fasteners and the like. The stops 48, 50 on each end of the rod 46 are preferably configured to engage with one or more protrusions 52, 54 that extend radially inwardly from an interior surface of the handle to prevent the rod 46 from sliding longitudinally beyond the respective protrusions 52, 54. Thus, when the thumb trigger 32 is pushed forward or distally by the user, the rod 46 also slides distally within the handle until the stop 50 at the distal end of the rod 46 abuts the distally located protrusions 54 within the handle or until the thumb trigger 32 is moved to the distal-most point in the longitudinal slot 34. The rod 46, having the proximal end 22 of the stylet 14 mounted thereto, is prevented from moving any further forward in the handle interior 20 and, as such, the distal end 24 of the stylet 14 cannot be advanced any further forward out of the distal end 17 of the shaft. Likewise, when the thumb trigger 32 is moved back or proximally towards the user, the rod 46 slides proximally within the handle interior 20 until the stop 48 at the proximal end of the rod 46 abuts the proximally located protrusions 52 within the handle interior 20 or until the thumb trigger 32 is moved to the proximal-most point in the longitudinal slot 34. The rod 46 is thus prevented from sliding any further backwards, thus signaling the user that the stylet 14 is fully retracted within the shaft 12.

Preferably, a biasing member, such as a spring 56, coaxially surrounds a portion of the proximal end 22 of the stylet where the stylet extends into the handle interior 20. The spring 56 is preferably positioned in front of the rod 46 so that the proximal end of the spring 56 abuts the distal stop 50 on the rod 46, while the distal end of the spring 56 abuts a distal end portion of the handle interior 20. In one example, the distal end of the spring 56 may abut or extend into the flare fitting 18 where the suture assembly 10 is mounted to the distal end 8 of the handle 4. The spring 56 preferably biases or urges the elongated rod 46 in a proximal direction within the handle interior 20 in order to force the stylet 14 (which is secured within and carried by the rod 46) in the retracted position. Thus, when the spring 56 is in a relaxed (e.g. an expanded state) as shown in FIG. 4, the stylet is biased rearwardly in the retracted position (and the thumb trigger 32 urged to slide to the proximal-most position in the longitudinal slot 34) until the user manually pushes the thumb trigger 32 forward (in a distal direction) to extend the stylet 14 out of the shaft 12. When the user pushes the thumb trigger 32 distally forward, the spring 56 is compressed as shown in FIG. 3, so that in order to keep the stylet 14 in the distally extended position, the user must manually maintain forward pressure or force upon the trigger 32 or, alternatively, slide the trigger 32 into the distally located lateral slot 38 to lock the stylet 14 in the extended position. If the thumb trigger 32 is not moved into the distally located lateral slot 38 to lock the stylet 14 in the extended position, release of the users thumb would allow for the spring 56 to return to its relaxed (expanded) position under the bias of the spring coil, thus pushing the elongated rod 46 and thumb trigger 32 proximally back towards the user so that the stylet 14 retracts back into the distal end 17 of the shaft.

As shown in FIGS. 3 and 4, the cylindrical member 42 may also be flanked on one or both of its distal and/or proximal ends by additional biasing members or springs 58, 60. The additional springs 58, 60 are held in place between the proximal and distal ends of the cylindrical member 42 and the proximal 48 and distal stops 50 of the rod 46, respectively. In one example, the additional biasing members 58, 60 help hold the cylindrical member 42 in a relatively centrally located position on the elongated rod 46 and also help to control any longitudinal sliding of the cylindrical member 42 relative to the rod 46 when the thumb trigger 32 is actuated by the user. In other words, the additional biasing members 58, 60 still allow for movement of the cylindrical member 42 relative to the elongated rod 46, but prevent the cylindrical member 42 from sliding loosely and freely in either a forward (distal) or backwards (proximal) direction within the handle interior 20 unless the user intentionally supplies a pushing force upon the thumb trigger 32 to initiate movement of the stylet 14 during a particular procedure.

The design of the handle 4, and in particular, the actuatable unit 40 that is longitudinally translatable within the handle interior 20 in order to control proximal and distal movement of the stylet 14, is preferably configured such that rotational movement of the stylet 14 is substantially, if not entirely, prevented. In one example, as shown in FIGS. 3, 3A and 4, one or both of stops 48 and/or 50 may have at least one channel or groove formed therein. More particularly, stop 48 may include a channel 49 formed therein, and similarly, stop 50 may include a channel 51 formed therein. Preferably, one or more corresponding surfaces that are formed in the handle interior engage the channels 49, 51 to prevent rotational movement of the actuatable unit 40 and of the stylet 14.

More specifically, the handle may include one or more raised surfaces that extend radially inwardly from an interior surface of the handle. As illustrated in FIGS. 3, 3A and 4, a raised rail or track 53 slides within or otherwise engages channel 49 near the proximal end 6 of the handle 4. Likewise, a raised rail or track 55 slides within or otherwise engages channel 51 near the distal end 8 of the handle 4. Thus, when the thumb-actuated trigger is moved in either a forward (distal) direction or a rearward (proximal) direction by the user, thus moving the actuatable unit 40 longitudinally within the handle interior (and correspondingly moving the stylet 14 within the shaft 12), the channels 49 and 51 slide longitudinally over the respective rails 53 and 55. The inter-engagement between the respective rail and channel surfaces, or, in other words, the raised rails extending into the corresponding channels, prevents rotational or pivotal movement of the actuatable unit within the handle interior. In this way, the longitudinal movement of the actuatable unit 40 (and of the stylet 14 carried by the actuatable unit 40) can be achieved by movement of the thumb-trigger 32, yet rotational movement of these structures is prevented.

In one example, when the thumb-actuated trigger 32 is moved into the lateral slots 36, 38 to lock the stylet 14 in either the distally extended position or the proximally retracted position, the stylet 14 preferably does not rotate within the shaft 12 nor does it rotate relative to the device 2. In other words, the thumb trigger 32 can be moved both longitudinally as well as laterally within the slots 34, 36 and 38 formed in the handle 4 to control longitudinal movement of the stylet 14 and also to lock the stylet in either an extended or retracted position, but the stylet 14 preferably does not rotate, turn, pivot, spin, swivel or the like within the shaft 12 or relative to the longitudinal axis 62 of the device 2 and/or relative to the shaft 12 despite movement of the thumb trigger 32 in any longitudinal and/or lateral direction.

As described above and as shown in FIGS. 5 and 6, the suture grasping portion 28 is formed in the distal end portion 24 of the stylet, and prior to performing a particular procedure, it may be desirable for the user to make note of the particular location of the suture grasping portion 28 relative to the remainder of the device 2, and in particular, relative to the shaft 12 and/or handle 4. For example, the user may observe whether the suture grasping portion 28 is formed on a particular side of the stylet 14 (and thus faces either left or right of center when the user holds the handle 4 in a position where the thumb trigger 32 is located directly on top of the handle 4) or whether the suture grasping portion 28 is formed on the top or bottom of the stylet 14 (and thus faces either upwards or downwards when the user holds the handle 4 in a position where the thumb trigger 32 is located directly on top of the handle 4). In any event, the user can recognize the position of the suture grasping portion 28 relative to the device 2 in any number of ways as the user sees fit, and in one particular example, the user may make note of the position of the suture grasping portion 28 relative to the location of the thumb actuated trigger 32 on the handle 4.

When a particular procedure is initiated and the suture assembly 10, including the suture grasping portion 28, is introduced into a patient's body and is thus concealed or hidden among the tissues or membranes, the user can still be confident of the location of the suture grasping portion 28 based on the position of the remainder of the device 2 that remains external to and is not concealed by the body or tissues. Using the example described above, the user may be confident of the location of the suture grasping portion 28 as the user manipulates the stylet 14 within the patient's body by noting the position of the thumb trigger 32 on the handle 4, for example, knowing that despite any longitudinal or lateral movement of the thumb trigger 32, there has not been any rotational movement of the stylet 14, and thus, no rotational change in position of the suture grasping portion 28 formed on the distal end 24 of the stylet. Any rotational or pivotal movement of the stylet 14 and suture grasping portion 28 that is desired by the user is preferably only accomplished by corresponding rotation or pivoting of the user's wrist, arm or hand that is being used to manipulate the device 2 during a given procedure.

While the preferred examples of the device 2 are described above, it is also contemplated that the device 2 described herein may be alternately configured such that rotational movement of the stylet 14 (and of the suture grasping portion 28 formed on the distal end thereof) may be achieved by lateral movement of the thumb-actuated trigger 32 (or by other suitable user-actuated mechanisms) if necessary or desired.

The above-described device 2 may be used for a variety of surgical procedures in accordance with the following exemplary methods. One exemplary use may include closure of a hernia repair, but one of skill will understand that the device 2 may have a variety of other uses in different procedures and in connection with different parts of the body. Manipulation of a suture 30 relative to a particular tissue, membrane, graft or a combination or multiple layers thereof, may be accomplished with the device 2 in several ways. In one example, a suture 30 may be pushed or pulled by the device 2 from a first side to a second side of a target tissue by grasping a free end of one or more sutures 30 and pushing the suture assembly 10 through the tissue or a perforation therein and releasing the suture 30 on the opposite (distal) side of the tissue. Alternatively, the suture assembly 10 may be first inserted or passed though the tissue or perforation therein, and then, the free end of the suture 30 grasped to allow the suture 30 to be pulled back though the tissue and released on the proximal side.

Prior to using the device 2 for manipulating a suture 30, the device 2 is preferably in a relaxed state with the stylet 14 biased in the retracted position within the shaft 12. In this position, the suture grasping portion 28 formed on the distal end portion 24 of the stylet is retracted within the shaft distal end 17 while the sharpened distal tip 26 remains exposed such that the tip 26 is extended beyond and located just distal to the distal end 17 of the shaft. As such, the pointed distal tip 26 facilitates easy insertion through the target tissue or a perforation therein, although, in the event that the tissue perforation is pre-existing, it is not necessary that the sharpened tip 26 of the stylet facilitate insertion through the tissue and the shaft 12 can simply be inserted through the tissue perforation.

By pushing the thumb-actuated trigger 32 forward or towards the distal end portion 8 of the handle 4, the stylet 14 is pushed distally, preferably so that at least the suture grasping portion 28 clears the distal end 17 of the shaft as FIG. 5 illustrates. To keep the stylet 14 in the distally extended position, the user must either maintain forward pressure on the thumb trigger 32 or alternatively, move the thumb trigger 32 into the distal lateral slot 38 to lock the stylet 14 in the extended position where the thumb trigger 32 can remain without manipulation or pressure from the user's thumb. With the stylet 14 in the extended position beyond the distal end 17 of the shaft, the suture grasping portion 28 is now exposed and available to grasp one or more sutures 30.

For example, the suture grasping portion 28 preferably includes a hook, a recessed channel, indentation, lip, overhang, catch, clasp, bevel, aperture, depression or similar structure that may be used to catch or snag and at least temporarily hold or retain a portion of a suture 30 or thread therein. As FIG. 5 illustrates, the suture grasping portion 28 includes a generally C-shaped hook 64 and further preferably includes a recessed portion 66 that is formed or carved into the distal end 24 of the stylet, such that once a suture 30 has been grasped by the distally located hook portion 64, the suture 30 is encouraged to slide into and remain positioned within the recess 66, even when the stylet 14 is in the extended position. In addition to the above-described configuration, it is also contemplated that the suture grasping portion 28 can be configured in a variety of ways that are also suitable for grasping and retaining a suture 30 therein as would be appreciated by one of skill in the art.

Once one or more sutures 30 have been grasped by the hook 64 and are retained therein, the user can move the thumb trigger 32 out of the distally located lateral slot 38 and back into the longitudinal slot 34 to unlock the stylet 14 from the extended position, or, if the stylet was not locked in position by the thumb trigger 32 in the distal lateral locking slot 38, the user can simply release his thumb from the trigger 32. Release of the trigger permits the spring 56 to move the elongated rod 46 (and stylet mounted therein) proximally so that the stylet 14 returns to the retracted position. As the stylet 14 is drawn back into the hollow shaft 12, the suture grasping portion 28 with a suture 30 held therein is also retracted back into the shaft 12. As shown in FIG. 6, the suture 30 becomes trapped between the recessed surface 66 of the suture-grasping portion 28 and the interior surfaces of the shaft 12. The user may retract the stylet 14 back into the shaft only partially so that at least part of the suture grasping portion 28 is still extended beyond the distal end 17 of the shaft, and, in this position, the suture 30 may be held within the hook 64 but may slide laterally or be re-positioned within the recess 66. Alternatively, the user may retract the stylet 14 fully so that the entire suture grasping portion 28 having a suture 30 threaded there through is pulled all the way back into the shaft 12 to secure and/or "trap" the suture 30 within the shaft 12, as FIG. 6 shows. In this position, the suture 30 preferably cannot be released from the suture grasping portion 28 and also cannot slide laterally within the recess 66 because the suture 30 is tightly captured and locked between the suture grasping portion 28 and the shaft 12.

In this retracted position, the device 2 is now loaded with a suture 30 and can be pushed forward through the target tissue and the suture released on the far or opposite side of the tissue. For example, with the suture assembly 10 having passed through the target tissue and securely holding a suture 30, it may be desirable to release the suture 30 from the device 2 on the opposite or distal side of the tissue. This may be accomplished by pushing the thumb trigger 32 distally to move the stylet 14 from the retracted position to the extended position. As the stylet 14 extends out of the distal end 17 of the shaft, the suture 30 can be released from the hook 64 on the opposite side of the tissue. Once released, the suture 30 can remain there undisturbed, or can be further manipulated, tied, or passed through additional target tissues as so desired by the user. With the suture released from its grasp and placed in a target tissue location, the stylet 14 may once again be retracted back into the shaft 12 by proximal movement of the thumb trigger 32 and the suture assembly 10 removed from the tissue.

Alternatively, if the suture assembly 10 had been passed through the target tissue prior to grasping the suture 30, the device 2 may be manipulated by the user to grasp and secure a suture within the suture grasping portion 28. Once the suture 30 is secured, the device 2 can be pulled back towards the user in a proximal direction in order to pull the suture 30 through the tissue where it can then be released on the proximal side. As with the prior example, the suture 30 can remain in place in this position undisturbed or it can be further manipulated if necessary or desired by the user. With the suture satisfactorily placed in position the suture assembly 10 may be removed from the tissue.

During a particular procedure, such as a hernia repair, the device 2 may be used to repeat one or more steps of the above-described method to place one or more sutures 30 to close the perforated tissues, membranes or grafts. The sutures 30 may be small gauge and preferably are large gauge such as "0" gage, and may be permanent, bio-absorbable, synthetic or comprised of biological material.

It is also contemplated that the handle 4 be constructed of separately molded components that are secured together. More specifically, the handle 4 may be constructed of similar or identical halves that are removably attachable to each other. As such, the handle portions can be separated, giving access to the handle interior 20. This allows the actuatable unit 40 and biasing members 56, 58 and/or 60 to be selectively removed and replaced as necessary or desired. In one example, this may be advantageous because one or more of the springs/biasing members 56, 58, 60 may be removed and replaced with others having a different size, stiffness, biasing force or the like, while also allowing the distal portion of the device 2 (including the stylet 14 and/or hollow shaft 12) to be replaced with others of different shapes or sizes, to accommodate different surgical procedures. In other words, the outer handle portions/halves can remain the same (thus reducing manufacturing costs, molds and/or materials) while other components of the device 2 can be customizable by the user.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together.

The invention claimed is:

1. A medical instrument for manipulating and placing a suture in body tissue comprising:
   a. a handle assembly comprising
      i. an elongated housing defining an interior chamber,
      ii. a longitudinal slot formed in the housing, the longitudinal slot having a proximal end and a distal end,
      iii. at least one lateral slot formed in the housing and extending from the longitudinal slot,
      iv. an actuation member moveable in the longitudinal slot between a proximal position and a distal position and moveable in the at least one lateral slot between a first lateral position and a second lateral position,
   b. a hollow shaft having a distal end portion and a proximal end portion removably coupled to the handle assembly, and a longitudinal axis extending between the proximal and distal end portions of the hollow shaft;
   c. a stylet extending within the hollow shaft and longitudinally slideable therein, the stylet having a distal end portion with a grasping member configured for engagement with a suture and a proximal end portion extending at least partially into the handle interior chamber, the stylet having a first position wherein the grasping member is retracted into the distal end portion of the hollow shaft and a second position wherein the grasping member extends distally beyond the distal end portion of the hollow shaft;
   wherein movement of the actuation member to the distal position within the longitudinal slot correspondingly moves the stylet to the extended position and movement of the actuation member to the proximal position within the longitudinal slot correspondingly moves the stylet to the retracted position;
   wherein the actuation member connects to a first member of the handle assembly and the stylet connects to a second member of the handle assembly, the first member being rotatable about the longitudinal axis on movement of the actuation member between the first and second lateral positions and slidable longitudinally on the longitudinal axis on movement of the actuation member between the proximal and distal positions; the second member being constrained against rotation about the longitudinal axis and being coupled with the first member to slide longitudinally of the longitudinal axis in response to movement of the actuation member between the proximal and distal positions, wherein movement of the actuation member between the first and second lateral positions does not impart rotational movement of the stylet relative to the hollow shaft.

2. The medical instrument of claim 1 wherein the handle assembly comprises a polymeric material.

3. The medical instrument of claim 1 wherein the grasping member comprises at least one of a hook, catch, clasp, indentation, recess, depression, bevel, aperture and lip.

4. The medical instrument of claim 1 wherein the actuation member comprises at least one of a trigger, knob, lever, rolling wheel, roller ball, button, slide and switch.

5. The medical instrument of claim 1 wherein the actuation member comprises a thumb-actuated slideable lever.

6. The medical instrument of claim 1 wherein the handle assembly comprises a first lateral slot and a second lateral slot formed in the housing.

7. The medical instrument of claim 6 wherein the first lateral slot extends from the proximal end of the longitudinal slot and the second lateral slot extends from the distal end of the longitudinal slot.

8. The medical instrument of claim 6 wherein movement of the actuation member into the first lateral slot locks the stylet in the retracted position and movement of the actuation member into the second lateral slot locks the stylet in the extended position.

9. The medical instrument of claim 1 wherein the handle assembly further comprises at least one biasing member.

10. The medical instrument of claim 9 wherein the at least one biasing member comprises a spring.

11. The medical instrument of claim 9 wherein the stylet is biased in the retracted position by the biasing member.

12. The medical instrument of claim 1 further comprising an actuatable unit disposed within the interior chamber.

13. The medical instrument of claim 12 wherein the actuatable unit has at least one channel formed therein and wherein the at least one channel is configured for slideable engagement with at least one protrusion extending radially inwardly from the interior chamber of the housing.

14. The medical instrument of claim 13 wherein the engagement between the at least one channel and the at least one protrusion is configured to prevent rotational movement of the stylet relative to the hollow shaft.

15. The medical instrument of claim 1, wherein the second member is a rod and the first member is coaxial with and extends circumferentially around the second member.

16. The medical instrument of claim 1, wherein relative longitudinal movement between the first and second members is limited by stops.

17. The medical instrument of claim 16, wherein relative longitudinal movement between the first and second members is opposed by biasing means.

18. A medical instrument for manipulating and placing a suture in body tissue comprising:
   a. a handle assembly comprising
      i. an elongated housing defining an interior chamber,
      ii. a longitudinal slot formed in the housing, the longitudinal slot having a proximal end and a distal end,
      iii. at least one lateral slot formed in the housing and extending from the longitudinal slot,
      iv. an elongated actuatable rod disposed within the housing interior chamber,
      v. a cylindrical member disposed within the housing interior chamber, and
      vi. an actuation member moveable in the longitudinal slot between a proximal position and a distal position and moveable in the at least one lateral slot between a first lateral position and a second lateral position, the actuation member engaging the elongated actuatable rod to impart proximal and distal longitudinal movements of the elongated actuatable rod within the housing;
   b. a hollow shaft having a proximal end portion coupled to the handle assembly and a distal end portion, and a longitudinal axis extending between the proximal and distal end portions of the hollow shaft;
   c. a stylet extending within the hollow shaft and longitudinally slideable therein, wherein the stylet is not rotationally moveable relative to the longitudinal axis, the stylet having a distal end portion with a grasping member and a proximal end portion extending at least partially into the housing interior chamber and removably coupled to the elongated actuatable rod, the stylet having a first position wherein the grasping member is retracted into the distal end portion of the hollow shaft and a second position wherein the grasping member extends distally beyond the distal end portion of the hollow shaft;

wherein movement of the actuation member to the distal position within the longitudinal slot correspondingly moves the stylet to an extended position and movement of the actuation member to the proximal position within the longitudinal slot correspondingly moves the stylet to a retracted position;

wherein the actuation member is coupled to the cylindrical member and the stylet is coupled to the elongated actuatable rod, the elongated actuatable rod extending through the cylindrical member, the cylindrical member being rotatable about the longitudinal axis on movement of the actuation member between the first and second lateral positions and slidable longitudinally on the longitudinal axis on movement of the actuation member between the proximal and distal positions; the elongated actuatable rod being constrained against rotation about the longitudinal axis and being coupled with the cylindrical member to slide longitudinally on the longitudinal axis in response to movement of the actuation member between the proximal and distal positions, wherein movement of the actuation member between the first and second lateral positions does not impart rotational movement of the stylet relative to the hollow shaft.

* * * * *